United States Patent [19]

Clark

[11] Patent Number: 5,167,924
[45] Date of Patent: Dec. 1, 1992

[54] FLOW THROUGH ASSAY APPARATUS AND PROCESS

[75] Inventor: Phillip Clark, Malden, Mass.

[73] Assignee: Millipore Corporation, Bedford, Mass.

[21] Appl. No.: 526,919

[22] Filed: May 22, 1990

[51] Int. Cl.$^5$ ............................................ G01N 31/00
[52] U.S. Cl. .................................... 422/58; 422/56; 422/57; 422/68.1; 422/61; 422/69; 422/101; 436/165; 436/169; 436/177; 436/807
[58] Field of Search ................. 422/56, 57, 58, 68.1, 422/61, 69, 101; 436/165, 169, 807, 177

[56] References Cited

U.S. PATENT DOCUMENTS

| 4,727,019 | 2/1988 | Valkirs et al. | 435/5 |
| 4,803,154 | 2/1989 | Uo et al. | 422/56 X |
| 4,976,926 | 12/1990 | Matkovich | 422/101 |
| 4,999,163 | 3/1991 | Lennon et al. | 422/101 X |

Primary Examiner—Robert J. Warden
Assistant Examiner—Stephanie Blythe
Attorney, Agent, or Firm—Andrew T. Karnakis; Paul J. Cook

[57] ABSTRACT

Assay apparatus is provided which includes a filter such as a porous membrane, a volume that can contain an absorbent and flexible means for reducing the volume in order to effect passage of liquid sample through the membrane and into the volume. The assay apparatus can be produced by a continuous manufacturing process.

1 Claim, 2 Drawing Sheets

FLOW THROUGH ASSAY APPARATUS AND PROCESS

BACKGROUND OF THE INVENTION

This invention relates to a method and apparatus for assaying a fluid sample to detect the presence or absence of a chemical or biochemical constituent in the sample or in the surrounding environment.

At the present time fluid samples are tested in a variety of apparatus for various constituents including specifically reactive pairs such as antibody-antigen pairs, enzyme-substrate pairs, D.N.A. fragment pairs, R.N.A. fragment pairs and the like. It is common practice to immobilize a reactant for the constitutent being tested on a support surface and then contacting the fluid sample with the coreactant. The constitutent is allowed to react with the coreactant to determine the presence, and, in some cases, the concentration of the constituent in the sample. Examples of assays which permit determination of the constituent concentration include the enzyme-linked immunosorbent assay (E.L.I.S.A.) and the radioimmunoassay (R.I.A.)

In these procedures, filter materials such as microporous or ultrafiltration membrane, nonwovens, papers, glass fibers, or other filter materials membranes provide a desirable immobilizing support for biologically active constituents since separation of the constituent for which the test is conducted can be easily effected. Examples of suitable membranes are disclosed in U.S. Pat. No. 4,066,512. Suitable apparatus utilizing these and other membranes to effect fluid sample assays are described in U.S. Pat. Nos. 4,246,339; 4,526,690; 4,632,901; 4,727,019 and U.S. Pat. No. 4,737,192. While each of these apparatus provides the capability of conducting accurate fluid assays, each of these apparatus suffer from the same deficiencies. The primary deficiency is that they comprise multipiece constructions which require that the apparatus pieces be formed in a batch mode of construction such as by injection molding. Thereafter the pieces are assembled to form the final apparatus. Due to their design and method of assembly, these apparatus are expensive to produce.

Accordingly, it would be desirable to provide apparatus for effecting assays which can be produced by a continuous process and are of unitary construction so that they can be mass produced without the need for manual labor. Furthermore, it would be desirable to provide such an apparatus which can effect either immediate reaction or permit an incubation period for the reactants. In addition, it would be desirable to provide such an apparatus which renders it possible to effect a multistep reaction process with variable incubation times being permitted for each step. Furthermore, it would be desirable to provide such an apparatus which can include one or a plurality of discrete reaction zones. Such apparatus would provide a desired economy in production and a desired flexibility in use of assay apparatus.

SUMMARY OF THE INVENTION

Figure 1:
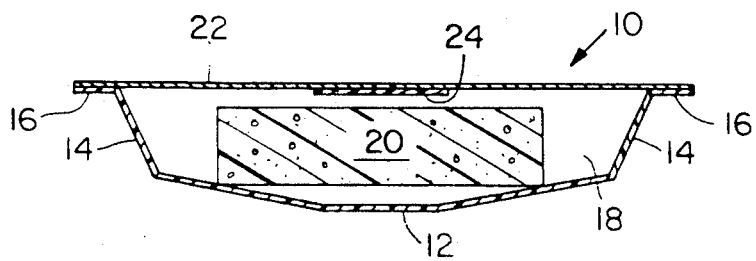
FIG. 1 is a side view of one assay apparatus of this invention.

The present invention provides an assay apparatus and process capable of conducting chemical or biochemical assays such as ELISA or RIA wherein reaction is effected rapidly or an incubation reaction period is utilized in one or multiple steps. The apparatus of this invention includes a porous filter membrane sealed to a membrane support as well as a flexible member adapted to effect evacuation of gas adjacent the membrane. The evacuation of gas adjacent the membrane promotes subsequent passage of a fluid sample through the membrane thereby to effect sample filtration. Fluid sample filtration occurs under the force of capillary action with an absorbent in contact with the membrane or by a vacuum induced by the gas evacuation. When a hydrophilic absorbent is utilized, it is positioned by moving the flexible member to evacuate air adjacent the bottom membrane surface and to contact the bottom membrane surface with the absorbent. Liquid sample placed on the top membrane surface then will pass through the membrane by capillary action caused by the membrane-absorbent contact.

In an alternative embodiment, the flexible member, the membrane and the membrane support are sealed together to define an enclosed air volume and a one-way valve is included on the membrane support. When the flexible member is moved toward the membrane, the valve opens and air is expelled from the enclosed volume. When the flexible member is moved away from the membrane, the valve closes and the pressure within the enclosed volume is reduced to the extent that liquid sample on the top membrane surface is forced through the membrane by virtue of the pressure gradient across the membrane.

In use, the fluid sample to be assayed is positioned on the membrane which can contain a complementary reactant to the material for which the assay if conducted and incubated for a time sufficient to effect the desired reaction. In some instances, it is desired that the sample immediately be filtered through the membrane, in which case an absorbent material which effects sample wicking contacts the membrane when the sample is positioned on the membrane or the vacuum is induced within the enclosed volume free of absorbent. In another aspect of this invention, a chemical reagent composition can be housed within an ampoule and Positioned within the absorbent. When it is desired to use the device, the ampoule is broken when the flexible member is flexed by hand, the flexible wall is moved toward the membrane so that absorbent contacts the membrane and the chemical reagent migrates through the membrane to be exposed to the surrounding atmosphere. This embodiment of the invention is capable of monitoring for the presence of specific reactants in the surrounding environment.

Reaction product in the membrane, if any, can be shown by any suitable technique. For use with E.L.-I.S.A. Procedures when the reagent and co-reactant are a specific antibody-antigen pair, a conjugate of an active enzyme with a biological material specific to the harvested reagent can be passed through the membrane, followed by washing as above described. A substrate-chromogen mixture specific to the enzyme is then passed through the membrane to develop visible color in the presence of harvested reagent. Preferably the test is performed with positive and negative controls in which control samples, (a) known to contain the reagent (positive) and (b) known to be free of reagent (negative), are passed through adjacent test wells and the control membranes compared with the test membrane(s).

DESCRIPTION OF SPECIFIC EMBODIMENTS

The apparatus of this invention is useful to effect an assay of discrete fluid samples or to assay the environment surrounding the apparatus. In one form of this invention, the membrane has bound to it a specific receptor such as an antibody, antigen, DNA strand, RNA strand, enzyme, enzyme substrate or the like which is specific for a complementary ligand in a manner well known in the art. A portion of the membrane surface can be hydrophobic which the remainder of the membrane surface is hydrophilic.

Figure 2:
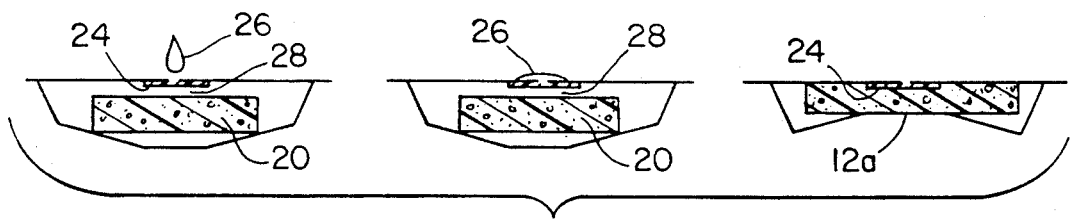
FIG. 2 illustrates the use of the apparatus of FIG. 1.

Referring to FIGS. 1 and 2, the assay apparatus 10 includes a flexible wall 12 which functions as a diaphragm formed integrally with side walls 14 which, in turn, are formed integrally with flanges 16. The flexible wall 12, side walls 14 and flanges 16 together form a well 18 to house an absorbent material 20. The flanges 16 are sealed about the entire periphery of the well 18 to a liquid impermeable member 22 such as a plastic film or an adhesive coated film so that the well 18 can be hermatically sealed. The liquid impermeable member 22 includes one or more holes so that a filter 24 can be sealed to the member 22. The flexible wall 12 can be made of an thin flexible material that can be flexed manually as described below such as polystyrene, aluminum foil or laminate. The flexible wall can be made from any thermoplastic material, or a component of multiple films as long as they are formable and can be hermatically sealed to member 22.

As shown in FIG. 2, liquid sample 26 is added dropwise to contact the membrane 24. The membrane can contain, entrapped therein particles such as latex particles having their surface made first with a conjugate adapted to bind a desired reactant in the sample. As shown in FIG. 2, the membrane 24 is separated from absorbent 20 by space 28. When the absorbent 20 is so-positioned, there is no driving force for the liquid sample 26 to be passed through the filter 24. If desired, the wall 12 can be flexed toward the membrane 24 to effect contact with the undersurface of the membrane prior to applying the liquid sample 26 to the membrane 24. In this case, the liquid sample will pass through the membrane immediately under capillary action. After incubation, if desired, is complete, the wall 12 is flexed to the position 12a so as to effect passage of the sample 26 through the membrane 24 leaving a filtrate, a bound reactant, exposed on the surface of or within the membrane 24 which can be detected by any conventional means such as ELISA or RIA. When it is desired to utilize the apparatus 10 of FIG. 1 by the method illustrated in FIG. 2 to detect a constituent in the atmosphere surrounding the apparatus 10, an ampoule 11 containing a chemical composite is included within the well 18. When the wall 12 is flexed toward membrane 24, the ampoule is broken and the chemical composition migrates through absorbent 20 through filter 24 and contacts the atmosphere 28. The chemical composition then changes characteristics such as color when contacted with a composition in the atmosphere to be detected such as organics such as ethylene oxide or formaldehyde or metal vapors such as mercury or gases such as carbon monoxide or nitrogen oxides.

Figure 3:
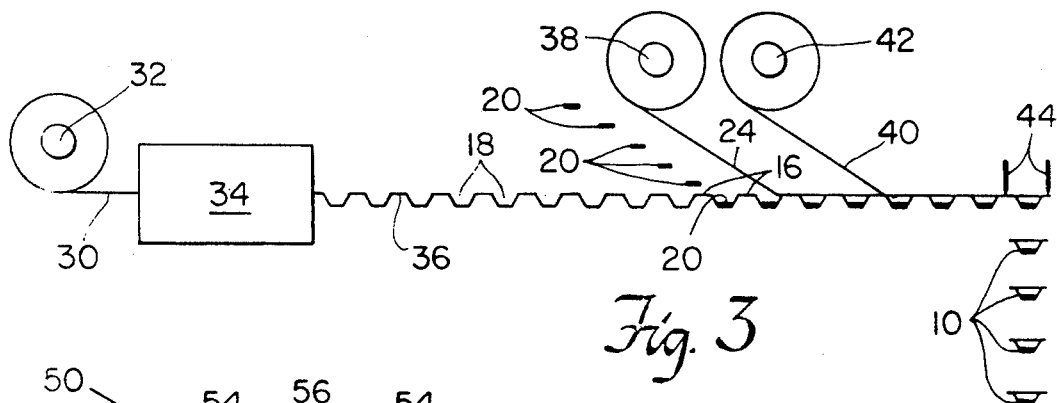
FIG. 3 illustrates a process for making the apparatus of FIG. 1.

Referring to FIG. 3, the apparatus 10 of FIG. 1 is formed continuously by Passing a flexible thermoplastic film 30 from roller 32 through a conventional vacuum or pressure forming step 34 to produce a continuous sheet 36 having a plurality of wells 18. Each of the wells 18 is filled with an absorbent 20 and the wells 18 containing the absorbent 20 is contacted with a porous filter 24 from roller 38 which is sealed in the flanges 16 of wells 18. A liquid impermeable cover 40 from roll 42 such as an aluminum foil laminated to a thermoplastic polymer is then heat sealed to the membrane 24 over the flanges 16. The cover 40 has holes spaced apart therein so that each assay apparatus 10 has a membrane 24 exposed on the top surface of the apparatus 10. Individual apparatus 10 then are formed by cutting the continuous sheet with conventional cutting apparatus such as knives 44.

Figure 4:
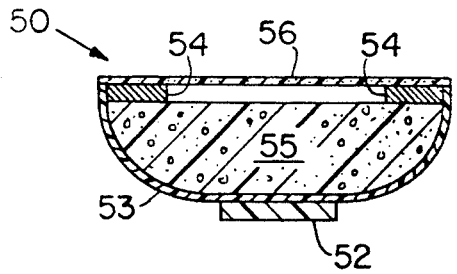
FIG. 4 is a side view of an alternative assay apparatus of this invention.
Figure 6:
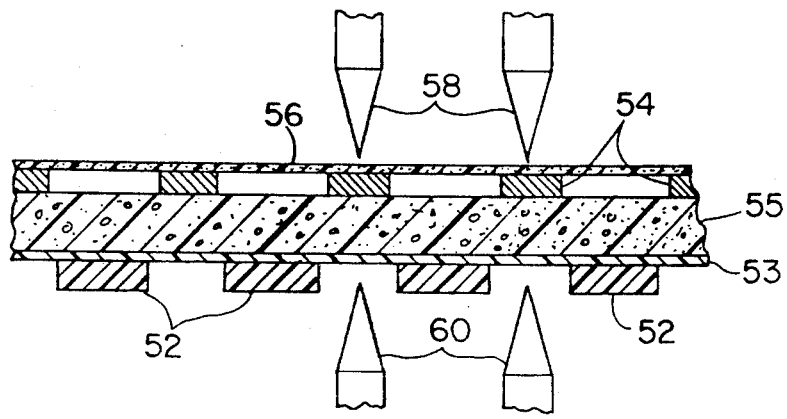
FIG. 6 illustrates a process for making the apparatus of FIG. 4.

Referring to FIG. 4, an apparatus of this invention is shown wherein the flexible wall is replaced by a movable plug. The assay apparatus 50 includes the plug 52, two spacers 54 which also can comprise a one piece disk as shown herein in cross section, an absorbent material 55 and a filter 56 sealed to the spacer 54. A cover having a hole can be included on the membrane 56 as discussed above with reference to FIGS. 1-3, if desired. As represented in FIG. 6, the apparatus 50 can be formed continuously by sealing the plug 52 to a sealing film 53 which, in turn, is sealed to absorbent 55. The film 53 and absorbent 55 can be unrolled from rollers continuously in the manner described above with reference to FIG. 3. The spacer 54, in spaced apart relationship, can be adhered to the absorbent 55 and the plug 52 can be bonded to film 53 such as by heat sealing adhesive or solvent bonding in spaced apart relationship. The filter 56 then is unrolled from a roller and sealed to the spacers 54. As in FIG, 3, a plurality of rows of assay apparatus can be formed continuously and simultaneously. Individual assay apparatus 50 can be formed by means of knife pairs 58 and 60.

Figure 5:
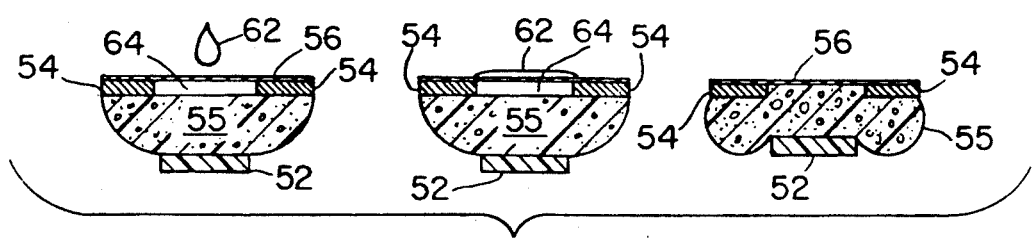
FIG. 5 illustrates the use of the apparatus of FIG. 4.

Use of the assay apparatus is shown in FIG. 5. The sample 62 is added to the top surface of filter 56, and, because of the presence of air space 64, the sample 62 does not pass through the filter 62. When it is desired to filter the sample 62, the plug 52 is manually moved toward filter 56 so as to move the absorbent 55 into space 64 and evacuate air therefrom. When the absorbent 55 contacts the filter 56, the liquid sample 62 is filtered through the filter 56 by capillary action.

Figure 7:
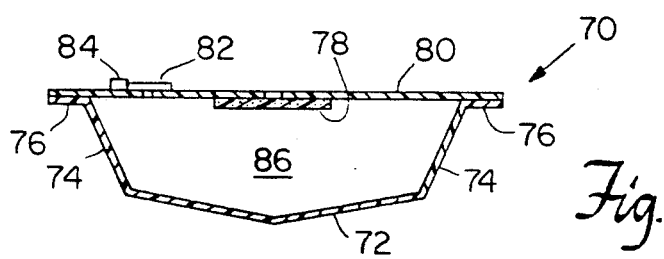
FIG. 7 is a side view of an alternative assay application of this invention.
Figure 8:
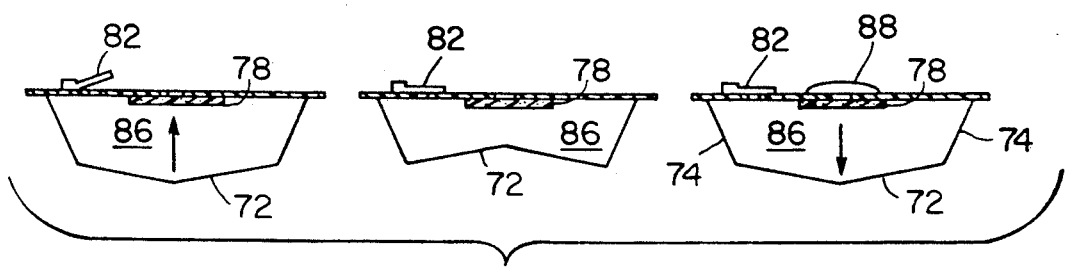
FIG. 8 illustrates a process for using the apparatus of FIG. 7.

An alternative embodiment of this invention which does not utilize an absorbent is shown in FIG. 7. The assay apparatus 70 includes a flexible wall, 72, side walls 74 and flanges 76. The filter 78 is sealed to a flexible cover 80. The cover 80 includes a valve 82 which covers a hole in flexible cover 80. The valve 82 is biased in a closed position and is attached to pivot about point 84 when pressure is increased within open volume 86. As shown in FIG. 8, when flexible wall 72 is moved toward filter 78, Pressure within volume 86 increases and valve 88 pivots open. When the movement of wall 72 stops, valve 82 returns to its closed biased position. When flexible wall 72 is moved away from filter 78, by a natural spring biasing formed in the wall 74 and 72 or by manually pressing side walls 74, pressure within volume 86 decreases thereby forcing liquid sample 88 through filter 78.

I claim:

1. Apparatus for conducting an assay for a constituent in a fluid sample which comprises:

a membrane filter a membrane support sealed to a portion of a first surface of said membrane filter a flexible layer secured to said membrane support and spaced apart from said membrane filter to form an open space between said membrane filter and said flexible layer, said open space being enclosed by said membrane filter, said membrane support and said flexible layer; said flexible layer being adapted to flex toward and away from said membrane filter, to evacuate gas from said open space and to promote passage of said fluid sample through said membrane filter and into the volume of said open space evacuated of said gas;

and an absorbent layer formed of a hydrophilic material positioned within a portion of said open space and positioned to contact said membrane filter when said flexible layer is flexed toward said membrane filter.

* * * * *